(12) United States Patent
Stephens (10) Patent No.: US 8,905,998 B2
(45) Date of Patent: Dec. 9, 2014

(54) CATHETER TUNNELER ADAPTER AND METHODS OF ASSEMBLY TO A CATHETER AND USE

(75) Inventor: John Stephens, Perkiomenville, PA (US)

(73) Assignee: Medical Components, Inc., Harleysville, PA (US)

( * ) Notice: Subject to any disclaimer, the term of this patent is extended or adjusted under 35 U.S.C. 154(b) by 1235 days.

(21) Appl. No.: 11/973,550

(22) Filed: Oct. 9, 2007

(65) Prior Publication Data

US 2008/0097409 A1 Apr. 24, 2008

Related U.S. Application Data

(60) Provisional application No. 60/852,847, filed on Oct. 19, 2006.

(51) Int. Cl.
| | |
|---|---|
| *A61M 25/16* | (2006.01) |
| *A61M 25/00* | (2006.01) |
| *A61F 11/00* | (2006.01) |
| *A61M 25/01* | (2006.01) |
| *A61B 17/34* | (2006.01) |
| *A61M 39/10* | (2006.01) |
| *A61B 17/32* | (2006.01) |

(52) U.S. Cl.
CPC ........ *A61B 17/3415* (2013.01); *A61M 25/0102* (2013.01); *A61M 2025/0037* (2013.01); *A61M 2039/1077* (2013.01); *A61M 2025/0034* (2013.01); *A61B 2017/320056* (2013.01); *A61M 39/105* (2013.01); *A61M 39/10* (2013.01); *A61M 25/0194* (2013.01)
USPC .............. 604/533; 604/523; 606/108

(58) Field of Classification Search
USPC ............ 604/158, 523–532, 533; 606/108
See application file for complete search history.

(56) References Cited

U.S. PATENT DOCUMENTS

| 4,326,516 A | 4/1982 | Schultz et al. |
| 4,405,163 A | 9/1983 | Voges et al. |

(Continued)

FOREIGN PATENT DOCUMENTS

| EP | 0157224 A2 | 3/1985 |
| EP | 0183396 A1 | 10/1985 |
| WO | WO 2005/099805 A1 | 10/2005 |

OTHER PUBLICATIONS

International Search Report dated Mar. 25, 2008 PCT/US07/021688 (4 pages).

(Continued)

*Primary Examiner* — Kami A Bosworth
*Assistant Examiner* — Imani Hayman
(74) *Attorney, Agent, or Firm* — Glenn M. Massina, Esq.; Fox Rothschild LLP (57) ABSTRACT

A catheter tunneling adapter including a generally elongated body having a proximal end, a distal end and a through passageway. The proximal end of the adapter is connectable both to a proximal hub of a stylet and subsequently to the distal end of a tunneler. The distal end of the adapter comprises a connector for connecting a plurality of proximal catheter tubes thereto, wherein the proximal end of one tube is affixed within the passageway at the adapter's distal end and the proximal end of the second tube is plugged by a plug extending distally from a free end of an elongate flexible arm that also extends distally of the adapter's distal end, such that the plug is offset laterally therefrom. The flexible arm and the affixed second tube end are deflectable toward the first tube to reduce the profile of the assembly during tunneling.

28 Claims, 7 Drawing Sheets

(56) References Cited

U.S. PATENT DOCUMENTS

| | | |
|---|---|---|
| 4,431,426 A | 2/1984 | Groshong et al. |
| 4,453,928 A | 6/1984 | Steiger |
| 4,832,687 A | 5/1989 | Smith, III |
| 5,190,529 A | 3/1993 | McCrory et al. |
| 5,360,407 A | 11/1994 | Leonard |
| 5,431,661 A | 7/1995 | Koch |
| 5,637,102 A | 6/1997 | Tolkoff et al. |
| 5,944,732 A | 8/1999 | Raulerson et al. |
| 6,423,053 B1 | 7/2002 | Lee |
| 6,453,185 B1 | 9/2002 | O'Keefe |
| 6,565,594 B1 | 5/2003 | Herweck et al. |
| 6,872,198 B1 | 3/2005 | Wilson et al. |
| 7,128,734 B1 | 10/2006 | Wilson et al. |
| 7,261,708 B2 | 8/2007 | Raulerson |
| 2004/0092863 A1 | 5/2004 | Raulerson et al. |
| 2004/0176739 A1 | 9/2004 | Stephens et al. |
| 2004/0230204 A1 | 11/2004 | Wortley et al. |
| 2005/0027282 A1 | 2/2005 | Schweikert et al. |
| 2006/0015130 A1 | 1/2006 | Voorhees, Jr. et al. |
| 2006/0095062 A1* | 5/2006 | Stephens ................ 606/191 |
| 2007/0078396 A1 | 4/2007 | Feeley et al. |
| 2007/0265597 A1* | 11/2007 | Schweikert et al. ......... 604/533 |

OTHER PUBLICATIONS

Written Opinion dated Mar. 25, 2008 PCT/US07/021688 (9 pages).
Notification of Transmittal of Intl. Preliminary Report on Patentability, PCT/US07/21688, mailed Jun. 8, 2009.

\* cited by examiner

CATHETER TUNNELER ADAPTER AND METHODS OF ASSEMBLY TO A CATHETER AND USE

CROSS REFERENCE TO RELATED APPLICATIONS

This application claims priority from Provisional U.S. Patent Application Ser. No. 60/852,847 filed Oct. 19, 2006.

FIELD OF THE INVENTION

The present invention relates to medical devices and more particularly to an adapter for a vascular catheter to facilitate subcutaneous tunneling thereof.

BACKGROUND OF THE INVENTION

Catheters for the introduction or removal of fluids may be located in various venous locations and cavities throughout the body of a patient for introduction of fluids to the body or removal of fluids from the body. Such catheterization may be performed by using a single catheter having multiple lumens. A typical example of a multiple lumen catheter is a dual lumen catheter in which one lumen introduces fluid and the other lumen removes fluid. An example of such a multiple catheter is the SPLIT-CATH® catheter, sold by Medical Components, Inc. of Harleysville, Pa.

Generally, to insert any catheter into a blood vessel, the vessel is identified by aspiration with a long hollow needle in accordance with the well known Seldinger technique. When blood enters a syringe attached to the needle, indicating that the vessel has been found, a thin guide wire is then introduced, typically through a syringe needle or other introducer device into the interior of the vessel. The introducer device is then removed, leaving the end portion of the guide wire that has been inserted into the vessel within the vessel and the opposing end of the guide wire projecting beyond the surface of the skin of the patient. At this point, several options are available to a physician for catheter placement. The simplest is to pass a catheter into the vessel directly over the guide wire. The guide wire is then removed, leaving the catheter in position within the vessel. However, this technique is only possible in cases where the catheter is of a relatively small diameter, made of a stiff material, and not significantly larger than the guide wire. For example, this technique may be used to insert small diameter dual lumen catheters into a patient. If the catheter to be inserted is significantly larger than the guide wire, a dilator device is passed over the guide wire to enlarge the hole. The dilator device is then removed, and the catheter is then passed over the guide wire into the vessel. The guide wire is then removed.

For chronic catheterization, in which the catheter is intended to remain inside the patient for an extended period of time, such as for weeks or even months, it is typically desired to subcutaneously tunnel the catheter using various tunneling techniques. The catheter is typically tunneled into the patient prior to inserting the catheter into the patient's vein. However, depending on the patient or the implanting surgeon's skill, there may be times when it is more advantageous to perform the tunneling after the catheter is implanted in the patient. For some catheters, though, such as multiple lumen catheters with a hub and with bonded luers on the proximal ends of the catheters, it is impractical to perform the tunneling after the catheter is installed in the patient.

An alternative installation procedure is available for installing the catheter that better suits the patient's needs and the surgeon's skills. Such an alternative catheter assembly is the multi-lumen catheter disclosed in U.S. patent publication No. US 2004/0092863. In order to be able to perform the tunneling after the distal end of the catheter assembly is inserted into the patient (termed retrograde tunneling), the proximal ends of each catheter must be attached to a tunneler device adapted to pull the proximal end of each catheter through the tunnel. After tunneling, the proximal ends of the catheters must be disconnected from the tunneler device and then connected to a catheter hub.

U.S. Patent Publication No. US 2004/0176739 is directed to a catheter tunneling adapter that allows for the simultaneous tunneling of the proximal ends of each catheter in a multi-lumen catheter assembly. The adapter is comprised of a generally elongated body having a distal end and a proximal end and a longitudinal axis extending therethrough between the distal end and the proximal end. The proximal end includes a connector for connecting a catheter tunneler thereto. The distal end comprises a connector for connecting a plurality of catheter lumens thereto. The publication also provides a method of inserting a catheter having a plurality of lumens into a patient. The method is comprised of inserting a distal end of each of the plurality of lumens into a blood vessel in the patient; connecting a proximal end of each of the plurality of lumens to a tunneling device; forming a subcutaneous tunnel with the tunneling device; drawing the proximal ends of each of the plurality of lumens simultaneously through the tunnel; disconnecting the tunneling device from the proximal ends of each of the plurality of lumens; and connecting the proximal ends of each of the plurality of lumens to a catheter hub component. Such a catheter hub component is disclosed in U.S. Pat. No. 7,261,708 that is mountable to a catheter's proximal end after tunneling thereof has been performed.

It would be desirable to provide the practitioner the option of inserting the distal catheter portion into the vasculature using a stylet rather than an introducer sheath. It would be desirable to provide an adapter that releasably connects the stylet with the catheter for vascular insertion, after which the stylet is removable. It would further be desirable for such an adapter to also provide for subsequent connection thereto of a tunneler.

BRIEF SUMMARY OF THE INVENTION

The present invention is an adapter that at its distal end is securable onto the ends of two (or more) lumens of a catheter to facilitate implantation thereof in a patient's vasculature, and is securable at its proximal end to, sequentially, a stylet and also a tunneler, so that while connected to the catheter's proximal end it permits releasable connection with a stylet for the guide wire to permit implantation of the distal portion in place in the vasculature, and then with a tunneler for subcutaneous tunneling of the proximal portion of the catheter. The adapter includes a body defining a through passageway from its proximal end to its distal end. The through passageway permits a stylet to be inserted through the adapter and into and through the first lumen of the catheter to extend to and beyond the distal end of the first lumen so that the guide wire is insertable through the catheter for precise vasculature implantation of the catheter. Preferably, the adapter is assembled to the catheter during manufacturing, and is shipped with a stylet already in position releasably secured to the adapter. Even more preferably, the adapter is affixed to the catheter. The adapter may be removed from the catheter lumen by severing the end of the catheter lumen and then discarded; further, the tunneler need not be separately removed from the adapter after tunneling since it will be discarded, as well.

In one embodiment, the adapter of the present invention is generally tubular with a through passageway extending from an entrance for connection to the stylet and tunneler and an exit for connection to the catheter proximal end, and is used with single-lumen catheters in a manner otherwise similar to that used with the previously described embodiment.

In another embodiment, the adapter is adapted for use with a catheter whose proximal end has at least two separate lumens defined in proximal tubes that are separate from each other. Having a generally tubular body with a through passageway as in the first embodiment set forth hereinabove, the body also includes a flexible arm of soft material that extends at a lateral offset distally of the distal end of the adapter body to a free end concluding in a plug that is disposed distally of the passageway exit and is offset laterally of the longitudinal axis of the through passageway. While a first proximal tube of the multilumen catheter is secured in the exit of the through passageway, a second proximal tube receives into its proximal end the plug of the flexible arm's free end. The flexible arm permits deflection toward the first catheter lumen to minimize the profile and facilitate pulling the catheter through the subcutaneous tunnel. The adapter may be removed from the catheter lumens by severing the ends of both proximal tubes of the catheter. The adapter may if desired have more than one flexible arm for a catheter with more than two proximal tubes.

The present invention also comprises an assembly of the adapter embodiments hereinabove described affixed respectively to a proximal end of a single-lumen catheter, or to the multiple proximal tubes of a multiple-lumen catheter. The assembly may include a stylet removably connected to the proximal passageway entrance of the adapter and extending therethrough.

The present invention also comprises a method of inserting a catheter using the adapters or the adapter/catheter assemblies hereinabove described. The method includes the steps of providing a catheter with at least one lumen having a proximal end; providing an adapter having a through passageway having a proximal entrance and a distal exit; affixing the adapter to the proximal end of the catheter; providing a stylet inserted through the proximal entrance of the adapter and through a lumen of the catheter affixed to the distal end of the adapter; removing the stylet; providing a tunneler adapted to be inserted into the proximal entrance of the passageway; either defining a subcutaneous tunnel with the tunneler, connecting the tunneler to the adapter and pulling the adapter/catheter assembly through the tunnel, or connecting the tunneler to the adapter and simultaneously tunneling subcutaneously and pulling the adapter/catheter assembly through the tunnel; severing the adapter from the proximal end of the catheter; and at least providing and connecting at least one fitting to the newly defined proximal end of the catheter.

The method may also include providing an adapter having a flexible arm extending distally therefrom and concluding in a distally extending plug spaced laterally from the longitudinal axis of the adapter; and affixing the plug sealingly in and to a second lumen of a multiple lumen catheter.

BRIEF DESCRIPTION OF THE DRAWINGS

The accompanying drawings, which are incorporated herein and constitute part of this specification, illustrate the presently preferred embodiment of the invention, and, together with the general description given above and the detailed description given below, serve to explain the features of the invention. In the drawings.

DETAILED DESCRIPTION OF THE PRESENT INVENTION

In the drawings, like numerals indicate like elements throughout. Certain terminology is used herein for convenience only and is not to be taken as a limitation on the present invention. The words "proximal" and "distal" refer to directions away from and closer to, respectively, the insertion tips of a catheter adapted to connect to the adapter of the present invention. The terminology includes the words above specifically mentioned, derivatives thereof, and words of similar import. The following describes a preferred embodiment of the invention. However, it should be understood based on this disclosure, that the invention is not limited by the preferred embodiment described herein.

Figures 1, 1A:
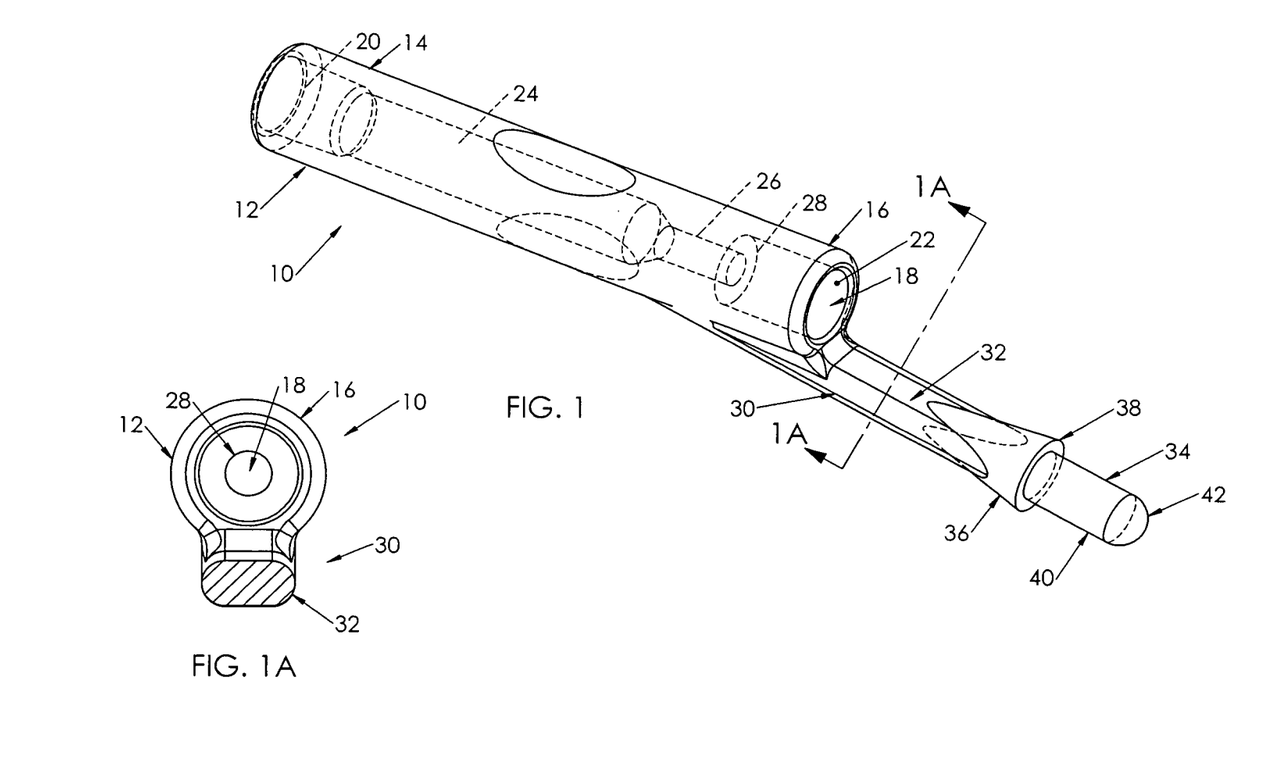
FIG. 1 is an isometric view of an adapter of the present invention.
FIG. 1A is an enlarged cross-sectional view taken along lines 1A-1A of FIG. 1.

A first embodiment of adapter 10 of the present invention is shown in FIGS. 1 to 7. Adapter 10 is shown in FIG. 1 to include body 12 having a proximal end 14, a distal end 16, a through passageway 18 extending through the body 12 from an entrance 20 at the proximal end 14 to an exit 22 at the distal end 16. The through passageway 18 also includes an intermediate, smaller diameter portion 24 and a transition portion 26 extending to the exit 22 and defining a distally facing ledge 28.

Figure 4:
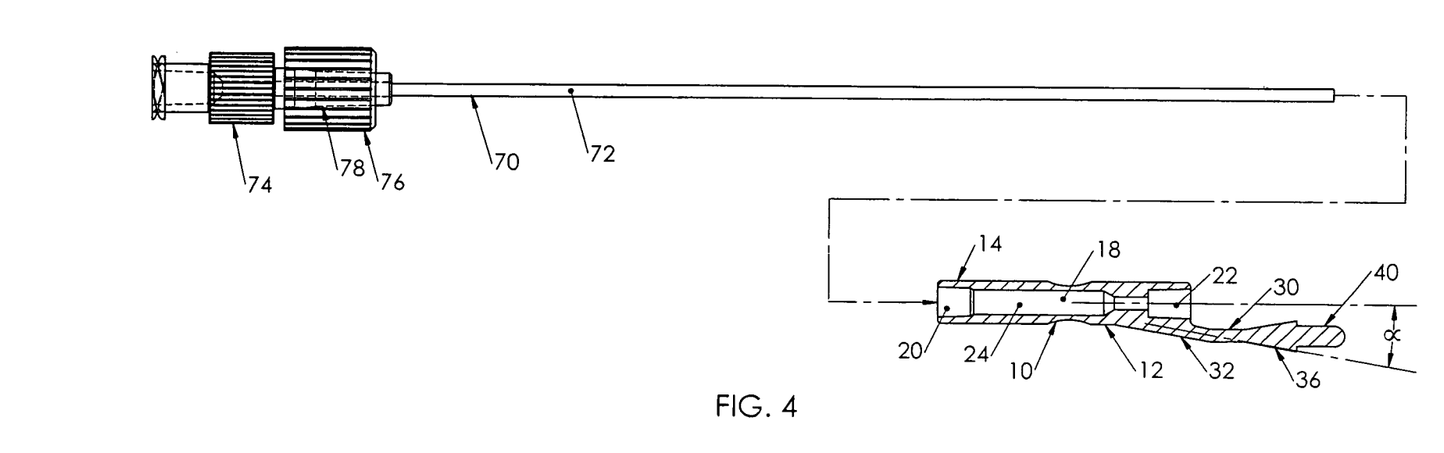
FIG. 4 is a longitudinal cross-sectional view of the adapter of FIGS. 1 to 3 exploded from a stylet to be releasably connected thereto and also shows a swivel lock affixed to the stylet's proximal hub.

Adapter 10 also includes a flexible arm 30 having an elongated section, strut or tether 32 extending to a free end 34 having a frustoconical enlargement 36 defining a distally facing ledge 38 distally from which extends a somewhat elongated plug 40 having a rounded, blunt tip 42. Preferably, the strut or tether 32 has a flattened cross-section (see FIG. 1A) facilitating deflection of the flexible arm toward the longitudinal axis defined by the through passageway 18, as will be described hereinbelow relating to subcutaneous tunneling of the catheter's proximal end. The strut or tether 32 is disposed at an angle α (see FIG. 4) of between 3 and 15 degrees with respect to the longitudinal axis of the adapter, and preferably about 10 degrees, and has a length sufficient to space distally the frustoconical enlargement 36 and plug 40 from the distal end 16 of body 12 when the flexible arm is deflected during tunneling. As is seen in FIG. 4, the enlargement 36 and the plug 40 then extend from the strut 32 generally parallel to the longitudinal axis. It is preferable that adapter 10 be made of soft biocompatible material like polyurethane, such as, for example, PELLETHANE® polyurethane sold by Dow Chemical Co. of Midland, Mich. and having a durometer such as about 80A. Preferably, modest gripping features may be provided on the outer surfaces of adapter body 12, which preferably is smooth and essentially free of threads or other discontinuities and has rounded edges at least after being affixed to a catheter as hereinbelow described.

Figure 2:
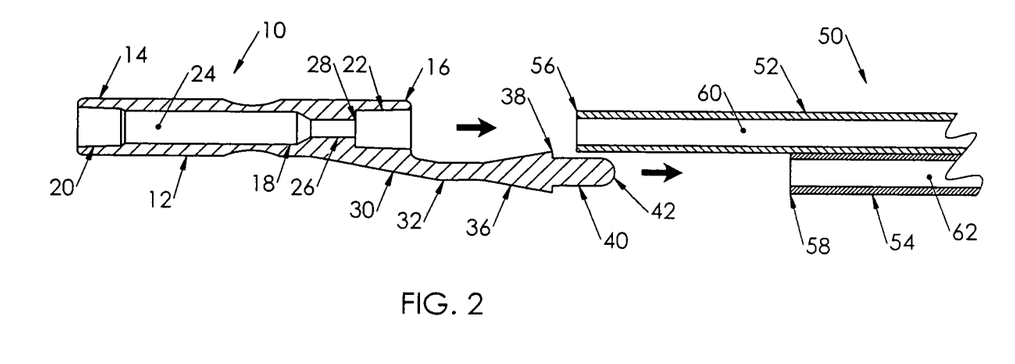
FIGS. 2 and 3 are longitudinal cross-sectional views of the adapter of FIG. 1, exploded from which are two lumens of a dual-lumen catheter in FIG. 2, and in FIG. 3 showing the adapter affixed to the two lumens.
Figure 3:
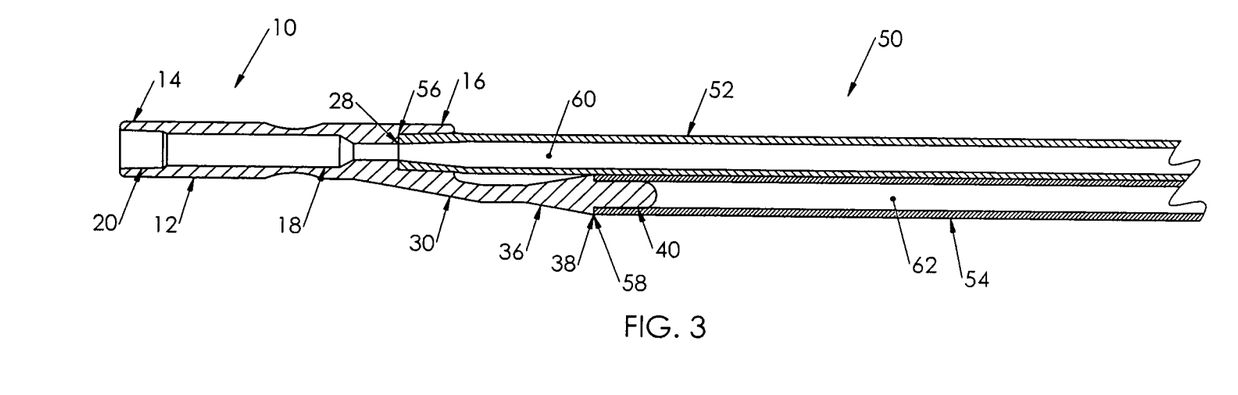

In FIGS. 2 and 3, adapter 10 is shown with a catheter 50 having a proximal end where the first and second proximal tubes 52,54 of the catheter are shown separated near their first and second proximal ends 56,58, such as by having been split apart for a selected length as disclosed in U.S. patent publication No. US 2004/0176739, and defining first and second lumens 60,62. Preferably, the length of the second proximal tube is shortened such as by trimming, such that the affixing of the first and second proximal tubes to the adapter permits the first and second proximal tubes to remain adjacent to each other.

During assembly of the adapter 10 to the catheter 50, first proximal tube 52 is insertable into passageway exit 22 until first proximal end 56 abuts ledge 28; second proximal tube 54 is insertable over plug 40 of flexible arm 30 until proximal end 58 abuts ledge 38. Preferably, plug 40 is so sized and shaped to be in a tight, friction fit within second lumen 62 to assuredly seal therewithin; further, preferably, the catheter proximal tubes are bonded or welded to adapter 10. Adapter 10 will later be removed from the catheter 50 by severing end portions of first and second proximal tubes 52,54 and then discarded. The maximum diameter of the frustoconical enlargement 36 is at least as large and preferably greater than the outer diameter of second proximal tube 54.

Figure 5:
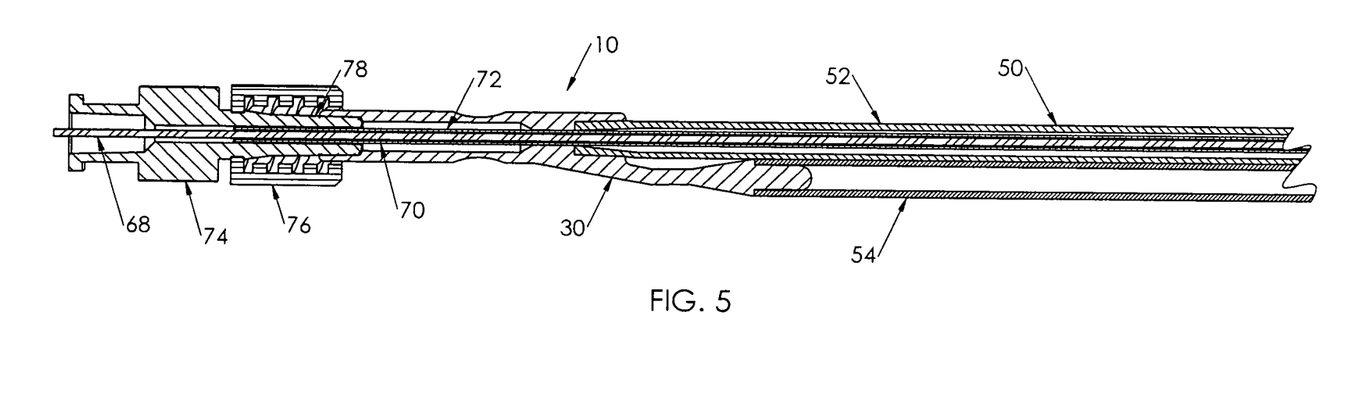
FIG. 5 is a longitudinal cross-sectional view of the adapter of FIGS. 1 to 3 affixed to the catheter with the stylet and a guide wire inserted through a passageway of the adapter and into a lumen of the catheter.

In FIGS. 4 and 5, a stylet 70 is shown having a relatively stiff, elongate stylet section 72 sufficiently long to extend completely through first lumen 60 of catheter 50 and beyond its distal tip (not shown), so that a guide wire 68 is easily insertable through the stylet and thus through the adapter and the catheter, for use in vascular placement of the catheter's distal portion, should the practitioner choose to use a stylet in vascular placement rather than use introducer sheath and dilator methods. Stylet 70 also has a proximal hub 74 distally of which is secured a freely rotatable swivel lock 76, with stylet hub 74 including a frustoconical distal projection 78. In FIG. 5, after stylet section 72 is inserted through adapter 10 from its proximal end, and extends into and through catheter first lumen 60, swivel lock 76 is adapted to be force fit over the outer surface of proximal end 14 of adapter 10, as the frustoconical distal projection 78 enters into the adapter's entrance 24 for releasable connection with the adapter, with stylet 70 being rotatable with respect to the catheter/adapter assembly. In FIG. 5, a guide wire 68 is shown inserted through the stylet 70, adapter 10 and catheter first lumen 60. Although not shown in FIG. 5, the guide wire distal end preferably extends through first lumen 60 and distally from the distal tip opening thereof and threaded into the second lumen distal tip portion that is longer than the first lumen, to project from the second lumen distal tip opening, as disclosed in U.S. Pat. No. 6,991, 625.

Figure 6:
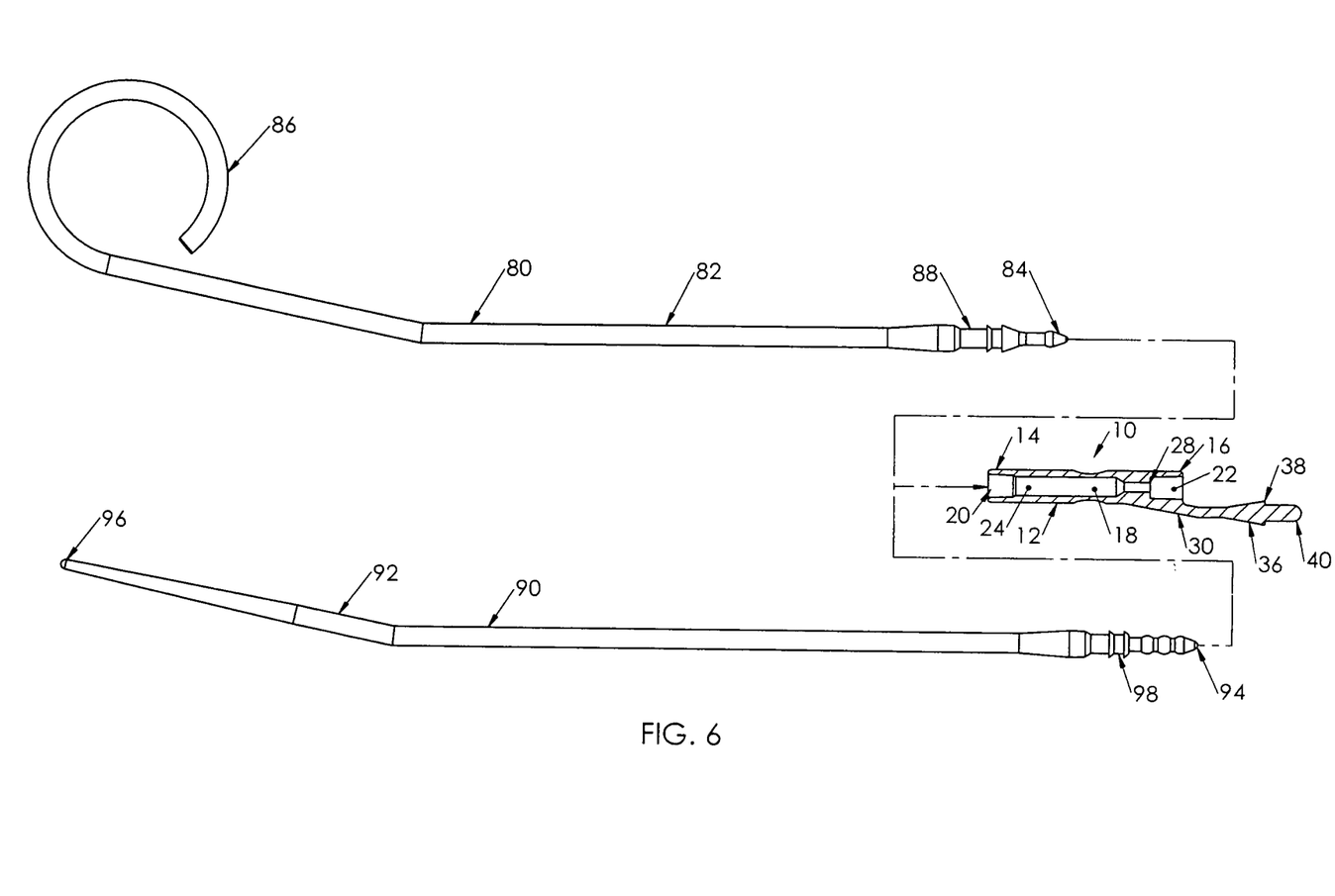
FIG. 6 is a cross-sectional view of the adapter of FIGS. 1 to 3, exploded from which are two styles of tunnelers that are releasably connectable to the adapter.
Figure 7:
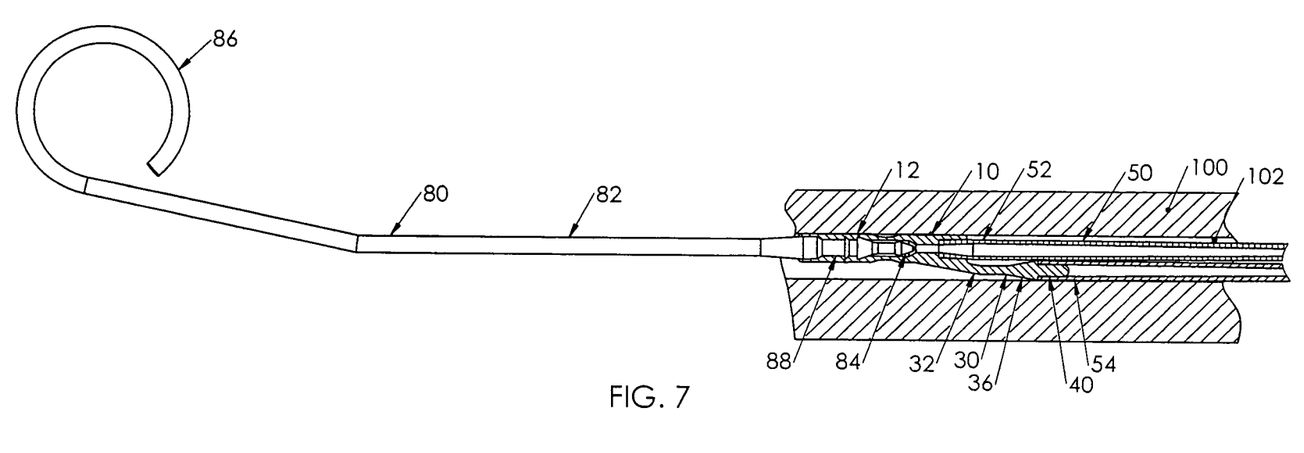
FIG. 7 is a longitudinal cross-sectional view of the adapter assembled to a tunneler of FIG. 6 with the adapter affixed to the two catheters and being pulled through a subcutaneous tunnel of a patient.

After the distal portion of the catheter 50 has been placed into the vasculature by use of the stylet (or by an introducer sheath/dilator approach), the stylet is removed and discarded, and the proximal portion of the catheter assembly now is to be tunneled. Referring now to FIGS. 6 and 7, two styles of tunnelers are shown, either one of which is connectable to the proximal end 14 of adapter 10. More conventional is tunneler 90, having a rigid shaft 92 extending from a blunt tunneling tip 96 to a blunt connection tip 94 adjacent to which is a connection section 98 having a plurality of barbs or annular projections that could be used to connect to a catheter lumen directly, but are also useful in establishing a firm connection with adapter 10. Also shown is another style of tunneler 80, the Raulerson Ring Handled Y Adapter Tunneler sold by Medical Components, Inc. of Harleysville, Pa. Tunneler 80 has a rigid shaft 82 having a blunt tunneling tip 84 and a manually grippable ring section 86 at its proximal end, and also includes a connection section 88 adjacent to its tunneling tip 84 for connection to a catheter lumen and also useful in connecting firmly to adapter 10 at proximal end 14 thereof.

Referring now to FIG. 7, tunneler 80 is shown after having been tunneled subcutaneously in patient 100 to define a tunnel 102 prior to connection to adapter 10. Then, tunneler 80 was inserted into proximal entrance 24 of adapter 10 forcibly connecting therewith via connection section 88. Tunneler 80 is shown after partially pulling adapter 10/catheter 50 proximal portion through tunnel 102.

It may be seen in FIG. 7 that flexible arm 30 of adapter 10, affixed to second proximal tube 54, is easily deflected toward first proximal tube 52 while being drawn through tunnel 102, thus facilitating the subcutaneous tunneling procedure. Frustoconical enlargement 36 of flexible arm 30 has a maximum diameter just greater than the outer diameter of second proximal catheter tube 54 so that there is no friction or snagging or dragging caused by the proximal edge of second proximal tube 54 at proximal end 58, and the sealed nature of the connection of plug 40 with second lumen 62 prevents any fluid, debris or air from entering second lumen 62.

After tunneling is completed, the proximal ends of first and second proximal catheter tubes 52,54 are severed adjacent to adapter 10, and the severed ends and the adapter are now discarded along with the tunneler. Now, the remaining portions of the catheter proximal tubes 52,54 enable placement thereonto of a hub such as is disclosed in U.S. Pat. No. 7,261,708 that is mountable onto a proximal catheter end having two proximal tubes, after tunneling of the catheter. Then, conventional extension tube assemblies are securable onto the exposed ends of the proximal tubes that protrude beyond the hub such as with conventional luer fittings to define a complete, implanted catheter assembly.

Figure 8:
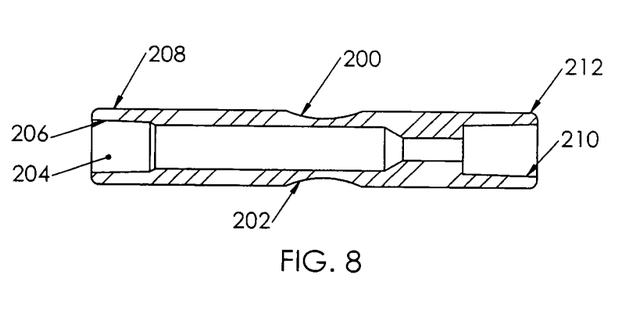
FIG. 8 is an isometric view of an alternate embodiment of adapter for a single-lumen catheter.

FIG. 8 illustrates another embodiment of adapter 200 that is useful with a single-lumen catheter. Adapter 200 has a body 202 with a through passageway 204 extending from an entrance 206 at proximal end 208 to an exit 210 at distal end 212. Unlike the adapter 10 of FIGS. 1 to 7, adapter 200 does not have or need a flexible arm, since the catheter has only a single lumen which would be inserted into exit 210 of adapter 200 and bonded or welded thereto. Since passageway 204 is aligned with the lumen of the catheter, a stylet is easily insertable into entrance 206 and into and through the lumen of the catheter. Again, as with adapter 10 the stylet enables a guide wire to be easily inserted through the adapter and the catheter for placement of the catheter's distal portion into the vasculature of a patient. Then the stylet is removed and a tunneler connected to the adapter at entrance 206 for tunneling of the adapter/catheter assembly.

Figure 9:
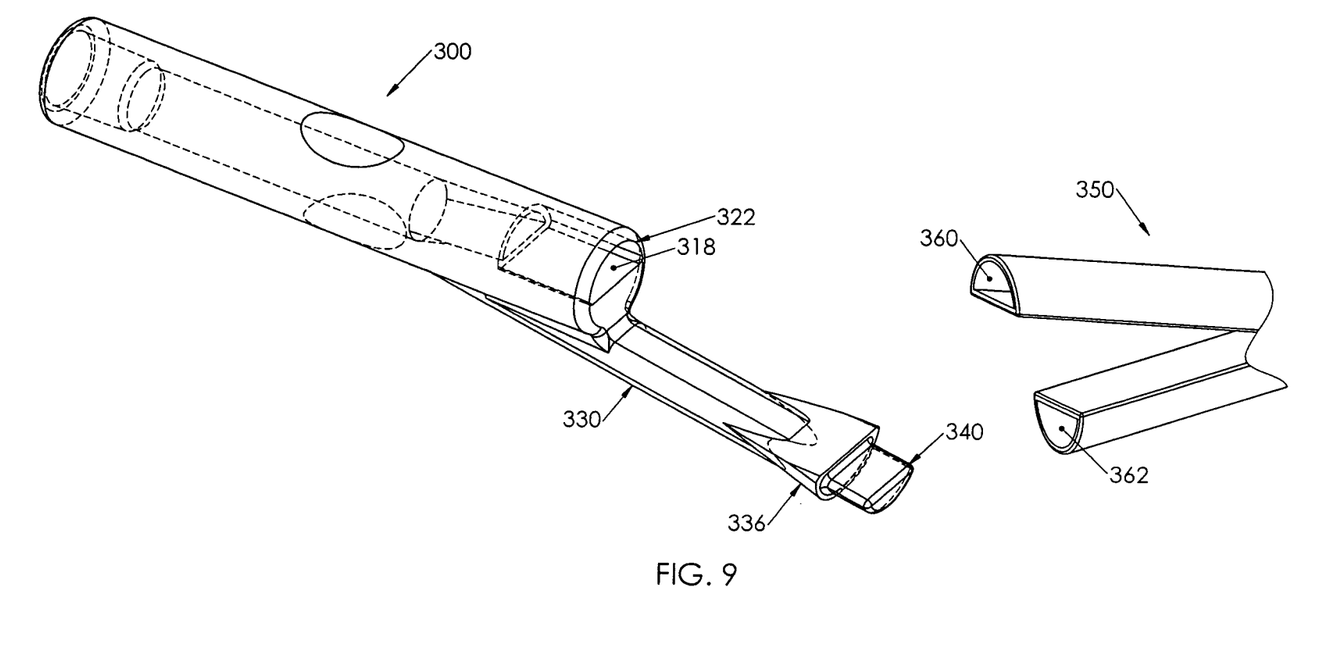
FIG. 9 is an isometric view of a third embodiment of adapter, wherein the adapter is modified at its distal end for use with a dual lumen catheter wherein the lumens have D-shaped cross-sections.

A third embodiment of adapter 300 is depicted in FIG. 9. Adapter 300 is modified at its distal end to accommodate a catheter 350 whose first and second lumens 360,362 have a D-shaped cross-section. Adapter passageway 318 has an exit 322 that is D-shaped in cross-section. Additionally, plug 340 on flexible arm 330 also has a D-shaped cross-section to be received sealingly into the second lumen's proximal end, and a correspondingly shaped enlargement 336.

Figure 10:
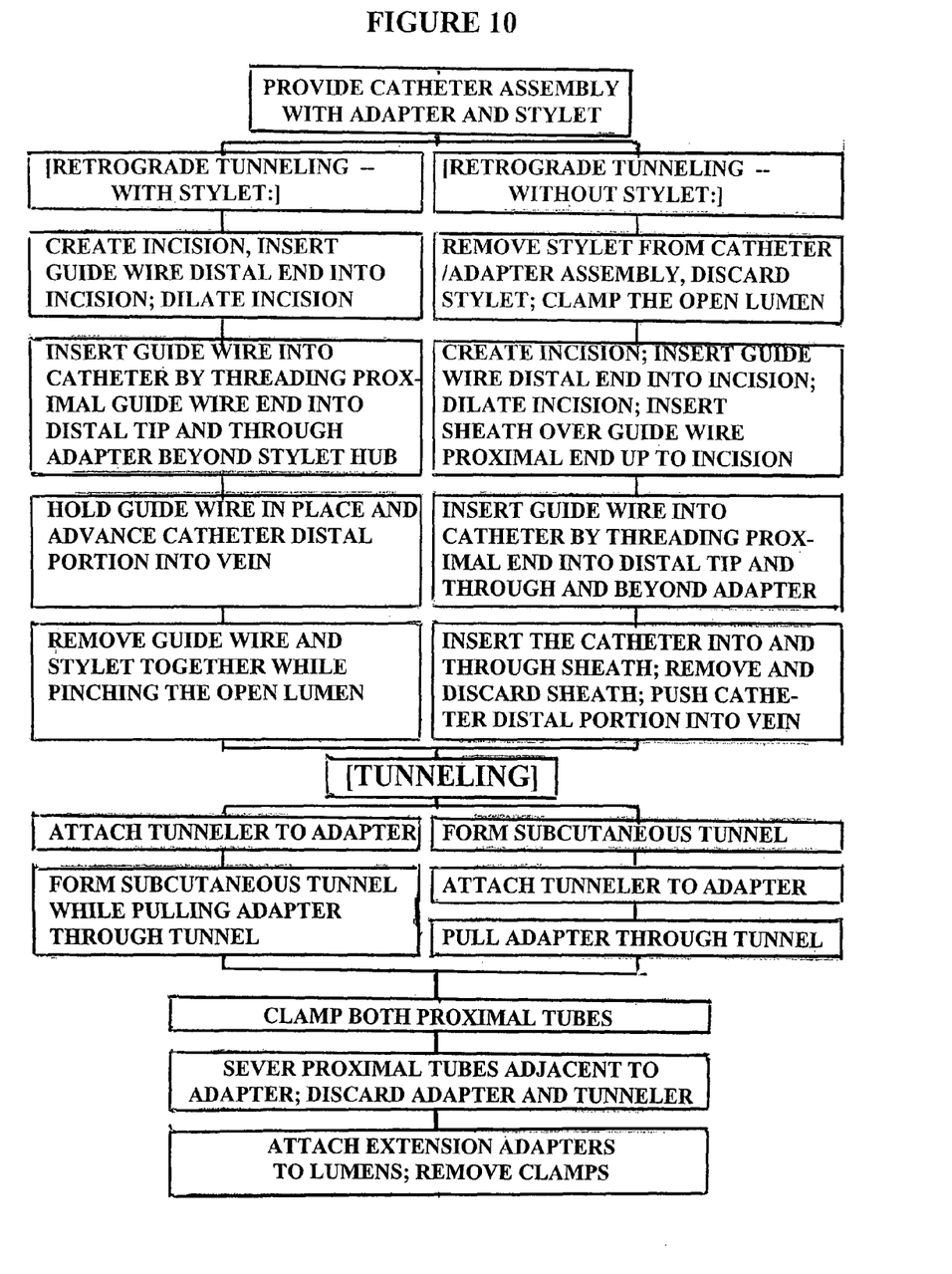
FIG. 10 is a flow chart illustrating the steps of inserting a catheter assembly into a patient using the adapter of FIGS. 1 to 3, according to the method of the present invention.

A flow chart is provided in FIG. 10 to set forth the method of using the adapter of the present invention, based on the embodiment of adapter 10 shown in FIGS. 1 to 3, and following a retrograde tunneling procedure. It is expected that the adapter of the present invention will be affixed to the proximal tubes 52,54 of the catheter 50 when received by the practitioner, and a stylet 70 is in position in the assembly releasably connected to the adapter 10. When received as an assembly by the practitioner, the assembly may either be inserted in the vasculature through use of the stylet, a dilator and a guide wire, or through use of an introducer sheath and dilator and guide wire. If the stylet approach is not to be used, the practitioner will remove and discard the stylet 70. If irrigation of the catheter is desired, a syringe (not shown) is attachable to the adapter or to the stylet.

In the method using an introducer sheath, the incision is formed in the blood vessel and a guide wire 68 (FIG. 5) is inserted therethrough and into the vasculature to the desired location. The introducer sheath (not shown) is placed into position over the guide wire's proximal end for the sheath's distal tip to extend to the incision. If enlargement of the vessel's incision is needed due to the diameter of the particular catheter to be implanted, a dilator (not shown) is placed onto the guide wire and is pressed through the sheath until the incision is dilated by the dilator's distal tip. The dilator is then removed from the sheath and the distal portion of the catheter assembly is inserted over the guide wire proximal end so that the guide wire extends through the second lumen's distal tip and then out of the second lumen and into and through the first lumen's distal tip, and the catheter is then inserted into the sheath and through the sheath's distal tip until the catheter's distal portion is within the vasculature; the sheath is then removed and discarded as the distal portion of the catheter assembly is positioned at the desired location in the vasculature by pushing it over and along the guide wire.

Following the dilator/sheath procedures to insert the distal catheter portion into position in the vasculature, and while the proximal catheter portion with adapter remains outside the patient, the practitioner then attaches the tunneler 90 to the adapter 10 and forms a subcutaneous tunnel and pulls the adapter and catheter proximal end through the tunnel 102; or the tunneler 80 is used to form the subcutaneous tunnel 102, then is attached to the adapter 10 and then pulls the adapter and the catheter proximal end through the tunnel 102. Thereafter, the catheter lumens 60,62 are clamped and the proximal tubes 52,54 are severed adjacent the adapter, and the adapter 10 and tunneler 80 or 90 and severed ends are discarded. Then a hub (not shown) is secured to the remaining lengths of the proximal tubes, and the extension tube assemblies are affixed to the newly defined proximal tube ends, and the clamps are removed from the lumens since the extension tube assemblies include associated clamps thereon.

In an alternate method, if the stylet 70 and guide wire are to be used to insert the catheter assembly, tunneling and post-tunneling procedures would be the same as hereinabove described. Insertion of the catheter assembly distal portion into the vasculature prior to tunneling would be accomplished as follows: a guide wire 68 is inserted into the incision and through the blood vessel to the desired site; a dilator is placed onto the guide wire proximal end and moved to the incision, and the vein access is dilated; the proximal end of the guide wire is then inserted into the stylet distal tip which is distal to the catheter's second lumen distal tip, and through the stylet distal tip and thus through the remainder of the stylet which is located within the first lumen 60 of the catheter 50, and through the adapter 10 and proximally outwardly of the stylet hub 74; the guide wire is held while the catheter assembly is then advanced into the vein and placed in the vasculature to the desired location. While the lumens 60,62 of the catheter assembly are pinched or clamped, the stylet and guide wire and dilator would then be removed and discarded, and the tunneling procedures described above would then be followed.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

What is claimed is:

1. A catheter tunneling adapter for connection to a proximal end of a catheter, comprising:
    an elongated body having a distal end and a proximal end and a tubular, open passageway extending through the body from the distal end to the proximal end, the passageway having an entrance at the proximal end and an exit at the distal end, and defining a longitudinal axis,
    wherein the proximal end is adapted to be removably connected to a catheter tunneler,
    wherein the distal end is adapted to be connected to at least one catheter lumen, and
    wherein the catheter has a first lumen and a second lumen defined in respective first and second proximal tubes of the catheter, and the adapter further includes a flexible arm that protrudes distally of the distal adapter end, offset laterally from the passageway exit at the distal end, and concludes in an elongate plug adapted to fit sealingly in a proximal end of the second proximal tube of the catheter,
    whereby the passageway permits insertion of a medical device through the adapter into the at least one catheter lumen when the tunneler is not connected to the adapter.

2. The catheter tunneling adapter according to claim 1, wherein the elongated body is generally tubular.

3. The catheter tunneling adapter according to claim 1, wherein the adapter is of unitary construction.

4. The catheter tunneling adapter according to claim 1, wherein the passageway entrance is sized to securely retain a distal end of a catheter tunneler.

5. The catheter tunneling adapter according to claim 1, wherein the passageway exit is sized to receive thereinto a proximal end of the at least one lumen of the catheter.

6. The catheter tunneling device according to claim 1, wherein the plug has a D-shaped cross-section, for insertion into a correspondingly D-shaped cross-section of the second lumen of the catheter, and the passageway exit also has a D-shaped cross-section to receive thereinto the correspondingly D-shaped cross-section of the first proximal tube of the catheter.

7. The catheter tunneling device according to claim 1, wherein the flexible arm includes an elongate section adapted to be easily deflectable toward the longitudinal axis of the passageway and the first proximal tube of the catheter during tunneling.

8. The catheter tunneling adapter according to claim 7, wherein the elongate section has a flattened cross-section oriented so that the flexible arm is easily deflectable toward a longitudinal axis of the through passageway.

9. The catheter tunneling adapter according to claim 1, wherein at least the flexible arm comprises a soft material facilitating flexing of the flexible arm.

10. The catheter tunneling adapter according to claim 9, wherein the adapter comprises polyurethane.

11. The catheter tunneling adapter according to claim 1, wherein the flexible arm includes an enlargement proximally of the plug that has a maximum diameter at least as great as an outer diameter of the second proximal tube and defines a distally facing abutment shoulder for abutment with the proximal end of the second proximal tube.

12. The catheter tunneling adapter according to claim 11, wherein the enlargement is frustoconical increasing in diameter proceeding distally to the plug.

13. The catheter tunneling adapter according to claim 1, wherein the elongate section of the flexible arm extends from an outer surface of the adapter body at an angle of between 3 and 15 degrees with respect to the longitudinal axis.

14. The catheter tunneling adapter according to claim 13, wherein the elongate section extends from the outer surface of the adapter body at an angle of about 10 degrees with respect to the longitudinal axis.

15. The catheter tunneling adapter according to claim 13, wherein the enlargement and the plug extend substantially parallel to the longitudinal axis.

16. A catheter tunneling adapter for connection to a proximal end of a multiple lumen catheter, comprising:
   an elongated body having a distal end and a proximal end and a longitudinal axis extending therethrough between the distal end and the proximal end,
   wherein the adapter comprises a passageway extending longitudinally through the elongated body from an entrance at the proximal end to an exit at the distal end,
   wherein the entrance is adapted to be removably connected to a distal end of a catheter tunneler,
   wherein the exit is adapted to be connected to a first proximal tube of a catheter through which extends a first lumen of the catheter,
   wherein the adapter further includes a flexible arm that protrudes distally from all other portions of the adapter and offset laterally from the passageway exit, and concludes in an elongate plug adapted to fit sealingly in a proximal end of a second proximal tube of the catheter and thus occlude a second lumen of the catheter.

17. The catheter tunneling device according to claim 16, wherein the flexible arm includes an elongate section adapted to be easily deflectable toward the longitudinal axis of the passageway and the first proximal tube of the catheter during tunneling.

18. The catheter tunneling adapter according to claim 17, wherein the elongate section has a flattened cross-section oriented so that the flexible arm is easily deflectable toward a longitudinal axis of the through passageway.

19. The catheter tunneling adapter according to claim 17, wherein at least the flexible arm comprises a soft material facilitating flexing of the flexible arm.

20. The catheter tunneling adapter according to claim 19, wherein the adapter comprises polyurethane.

21. The catheter tunneling adapter according to claim 16, wherein the flexible arm includes an enlargement proximally of the plug that has a maximum diameter at least as great as an outer diameter of the second proximal tube and defines a distally facing abutment shoulder for abutment with the proximal end of the second proximal tube.

22. The catheter tunneling adapter according to claim 21, wherein the enlargement is frustoconical increasing in diameter proceeding distally to the plug.

23. The catheter tunneling adapter according to claim 16, wherein the elongate section of the flexible arm extends from an outer surface of the adapter body at an angle of between 3 and 15 degrees with respect to the longitudinal axis.

24. The catheter tunneling adapter according to claim 23, wherein the elongate section extends from the outer surface of the adapter body at an angle of about 10 degrees with respect to the longitudinal axis.

25. The catheter tunneling adapter according to claim 24, wherein the enlargement and the plug extend substantially parallel to the longitudinal axis.

26. An assembly of the adapter of claim 16 and dual-lumen catheter affixed thereto at the distal end of the adapter.

27. The assembly of claim 26, further including a stylet extending into the entrance and through the assembly, and having a proximal hub removably affixed to the adapter proximal end.

28. A catheter tunneling adapter for connection to a proximal end of a multiple lumen catheter, comprising:
   an elongated body having a distal end and a proximal end and a longitudinal axis extending therethrough between the distal end and the proximal end,
   wherein the adapter comprises a passageway extending longitudinally through the elongated body from an entrance at the proximal end to an exit at the distal end,
   wherein the entrance is adapted to be removably connected to a distal end of a catheter tunneler,
   wherein the exit is adapted to be connected to a first proximal tube of a catheter through which extends a first lumen of the catheter,
   wherein the adapter further includes a flexible arm that protrudes distally of the distal adapter end, offset laterally from the distal end, and concludes in an elongate plug adapted to fit sealingly in a proximal end of a second proximal tube of the catheter and thus occlude a second lumen of the catheter, and
   wherein the flexible arm includes an enlargement proximally of the plug that has a maximum diameter at least as great as an outer diameter of the second proximal tube and defines a distally facing abutment shoulder for abutment with the proximal end of the second proximal tube, and the enlargement is frustoconical increasing in diameter proceeding distally to the plug.

* * * * *